United States Patent

Batchelor

[11] Patent Number: 5,997,474
[45] Date of Patent: Dec. 7, 1999

[54] VAGINAL SPECULA

[75] Inventor: Kester Julian Batchelor, Burnham-on-Sea, United Kingdom

[73] Assignee: Smiths Industries Public Limited Company, London, United Kingdom

[21] Appl. No.: 09/252,483

[22] Filed: Feb. 18, 1999

[30] Foreign Application Priority Data

Feb. 23, 1998 [GB] United Kingdom .................... 9803588

[51] Int. Cl.$^6$ ............................ A61B 1/32; A61M 29/00
[52] U.S. Cl. ............................ 600/220; 600/222
[58] Field of Search .................... 600/220, 221, 600/222, 224, 225, 223, 210, 184

[56] References Cited

U.S. PATENT DOCUMENTS

| | | | |
|---|---|---|---|
| 1,090,746 | 3/1914 | Nourse | 600/220 |
| 2,672,859 | 3/1954 | Jones | 600/220 |
| 3,528,409 | 9/1970 | Bruder | 600/220 |
| 4,385,626 | 5/1983 | Danz | 600/220 |
| 4,899,734 | 2/1990 | Gelley | 600/220 |
| 5,179,937 | 1/1993 | Lee | 600/220 |

FOREIGN PATENT DOCUMENTS 407357  1/1991  European Pat. Off. ............... 600/220

*Primary Examiner*—Paul J. Hirsch
*Attorney, Agent, or Firm*—Pollock, Vande Sande & Amernick

[57] ABSTRACT

A vaginal speculum has two hinged arms forming jaws at one end, and handles at the opposite end. A locking bar of a soft plastics material is pivotally mounted at one end on one of the handles, its other end projecting through an aperture in the other handle. The aperture has two portions of the aperture of different widths. One portion is wider than the locking bar, so that the bar can slide freely through the aperture to enable the separation of the jaws to be adjusted. The other portion of the aperture is slightly narrower than the locking bar so that the bar can be pushed into this narrower portion at any separation of the jaws to lock the arms in position.

7 Claims, 1 Drawing Sheet

VAGINAL SPECULA

BACKGROUND OF THE INVENTION

This invention relates to vaginal specula.

Vaginal specula are used to enlarge the passage through the vagina for gynaecological examination, sampling or treatment. The specula usually comprise two angled arms pivoted with one another to form jaws at one end and handles at the other end. The jaws can be separated by squeezing together the handles. The speculum often has some means by which the two jaws can be held in their separated state, so that the handles can be released once the passage has been enlarged sufficiently. One way of achieving this is by means of a ratchet arrangement, as in the speculum sold by SIMS Portex Limited of Hythe, Kent, England under the trade mark Cytospec. Another arrangement described in EP 407357 involves a pin fixed with one arm, which moves into and locks with a triangular slot in the other arm when the handles are squeezed together. Such an arrangement, however, only locks in one position and does not enable the user to select the degree of enlargement needed.

BRIEF SUMMARY OF THE INVENTION

It is an object of the present invention to provide an improved vaginal speculum.

According to the present invention there is provided a vaginal speculum comprising two arms hinged with one another at a point along their length and forming a pairs of jaws on one side of the hinge point and a pair of handles on the opposite side of the hinge point arranged such that the jaws can be separated by squeezing together the handles, one handle supporting one end of an elongate locking member the other end of which projects through an aperture in the other handle, the aperture having a first portion shaped to allow free passage therethrough of the elongate member and a second portion shaped to grip the elongate member such as to lock the arms with one another, and the elongate locking member being manually displaceable between said first and second portions at different positions of the arms so that they can be locked in different positions.

The elongate locking member is preferably pivotally mounted with the one handle. The pivotal mounting of the locking member may have sufficient friction to hold it in position against its weight. Alternatively, the elongate member may be fixedly mounted with the one handle, the elongate member being bendable. The elongate locking member is preferably of a softer material than the arms and may be a bar of rectangular section. The width of the first portion of the aperture is preferably wider than the bar, the width of the second portion being narrower than the bar.

A vaginal speculum according to the present invention, will now be described, by way of example, with reference to the accompanying drawings.

DETAILED DESCRIPTION OF THE PREFERRED EMBODIMENT

The speculum comprises two moulded arms 1 and 2 of a transparent rigid plastics material, such as SAN, polystyrene or ABS, and a rigid, elongate locking member or bar 3 of a slightly softer plastic material, such as polypropylene or PVC.

Figure 1:
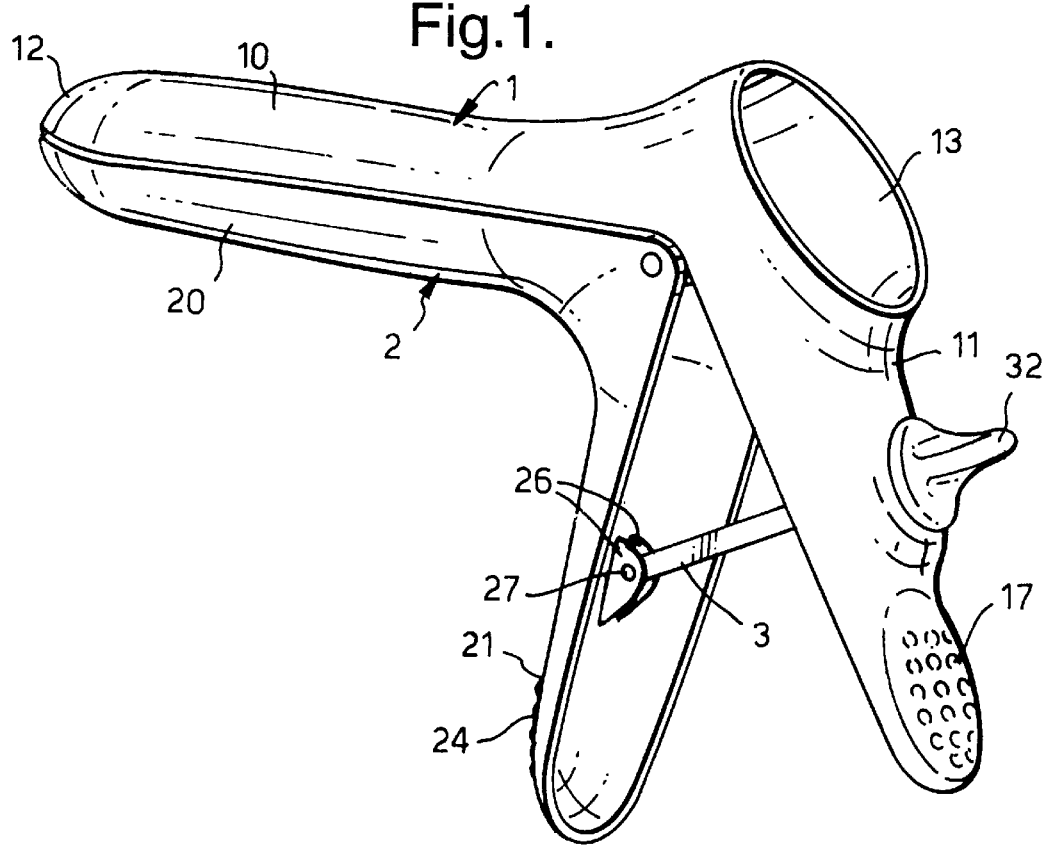
FIG. 1 is a perspective view of the speculum.
Figure 2:
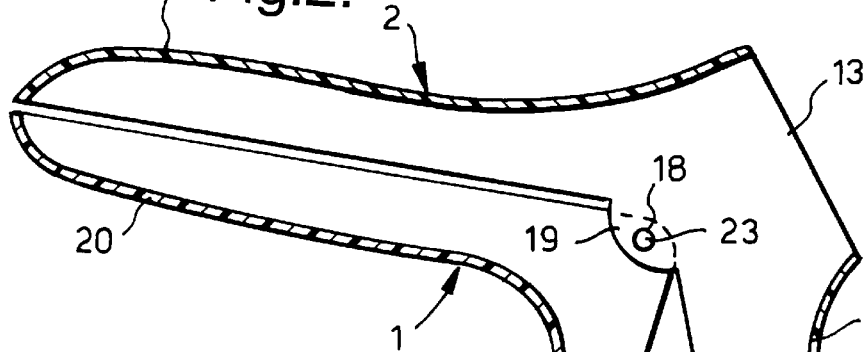
FIG. 2 is a sectional side elevation view of the speculum.
Figure 3:
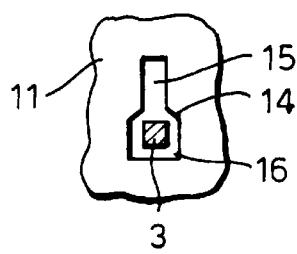
FIG. 3 is an end view illustrating a part of the speculum.

The upper arm 1 is angled approximately midway along its length at an angle of about 120 degrees to divide the arm into a forward portion forming a jaw 10 and a rear portion forming a handle 11. The jaw is about 100 mm long with a shape of a semicylindrical shell and having a rounded forward end or nose 12. The handle 11 has a generally convex external profile and a concave internal profile. A large oval aperture 13 extends through the handle 11 at its forward end, where the arm is angled, through which observations or procedures can be performed. Approximately midway along its length, the handle 11 has a second, smaller elongate locking aperture 14, aligned axially of the handle. As shown in FIG. 3, locking aperture 14 is divided into two portions: a forward, narrow portion 15 and a wider, rear portion 16, the purpose of which will become apparent later. The rear end of the handle 11 is flattened and roughened to form a thumb grip region 17.

The second, lower arm 2 is similarly divided into a forward jaw 20 and a rear handle 21, which are angled relative to one another at a sharper angle of about 90 degrees, so that when the two jaws 10 and 20 are brought together, the handles 11 and 21 diverge at an angle of about 30 degrees. The lower arm 2 has a generally convex external profile and a concave internal profile. In the corner between the jaw 20 and handle 21, the arm 2 has two pivot pins 23, which project inwardly, towards one another, from opposite sides of the arm. These pins 23 engage in holes 18 in respective bearing plates 19, which project from the upper arm 1 inside the lower arm. The rear end of the handle 21 has a roughened region 24 on its outside to improve grip by the user's fingers. About midway along the handle 21, on its inner, concave surface, there is a pivotal mounting 25 provided by two parallel, closely spaced axially-oriented mounting plates 26 projecting perpendicularly from the inner surface of the handle. The plates 26 support opposite ends of a short, transversely-extending axle 27. The plates 26 may have shallow projections (not shown) to aid alignment of the components during automatic assembly.

The spacing between the plates 26 is sufficient to receive one end of the locking bar 3, which has a bearing hole 30 through which the axle 27 extends so that the bar can be swung up or down on the axle. Preferably, the rotatable joint of the locking bar 3 has sufficient friction to hold the bar in position, so that the bar will not fall under its own weight but must be pushed by the user. This is helpful in enabling the speculum to be used in any orientation. The locking bar 3 is of rectangular section and extends through the locking aperture 14 in the upper handle 11, projecting a short distance beyond the handle where the bar is terminated with an enlarged finger grip 32. As shown in FIG. 3, the cross-section of the locking bar 3 is selected such that its lateral dimension is smaller than that of the wider, rear portion 16 of the aperture but is slightly wider than that of the forward, narrow portion 15. The relative dimensions of the locking bar 3 and the forward portion 15 of the aperture, and the relatively soft nature of the material of the locking bar 3 are such that the bar can be pushed into the narrow portion 15 where it is firmly gripped by the sides of the aperture. In this way, the locking bar 3 can move freely along its length in the wider portion 16 of the aperture 14 but can be locked against movement along its length by pushing it into the narrower portion 15.

In use, the handles 11 and 21 are initially fully separated so that the jaws 10 and 20 are closed together, presenting a generally rounded nose, for insertion in the vagina. The jaws 10 and 20 of the speculum are then inserted in the usual way to the desired position. The handles 11 and 21 are then squeezed together by gripping the regions 17 and 24 between the thumb and finger, until the desired enlargement of the vagina is produced. The jaws 10 and 20 can now be locked in this position simply by pushing the finger grip 32 on the locking bar 3 up, so that the bar enters the narrow part 15 of the aperture 14. Examination, sampling or treatment can then be carried out through the aperture 13 and between the separated jaws 10 and 20.

This arrangement has the advantage that the jaws 10 and 20 can be locked in different positions, thereby avoiding the need to apply excessive pressure when this is not needed. The locking can be achieved noiselessly, thereby avoiding the disconcerting clicking produced by some ratchet-locked specula. The speculum can be easily made at low cost so that it can be provided as a single-use, disposable item. Instead of having a rigid, pivoted locking bar, the bar could be fixedly mounted on the handle and the necessary movement of the free end of the bar could be achieved by making the bar bendable, while still permitting locking in any position. It will be appreciated that various modifications are possible to the speculum, for example, it could include a spring to urge the jaws to a closed or open position.

What I claim is:

1. A vaginal speculum comprising: two arms; a hinge between said two arms at a point along their length such that said two arms are formed into a pair of jaws on one side of said hinge and a pair of handles on an opposite side of said hinge arranged such that said jaws can be separated by squeezing together said handles; an elongate locking member having a first end and a second end; a support for said first end of said locking member on one of said handles; an aperture in the other of said handles, said second end of said elongate locking member extending through said aperture, and said aperture having a first portion shaped to allow free passage therethrough of said locking member and a second portion shaped to grip said locking member such as to lock said arms with one another, said locking member being manually displaceable between said first and second portions of said aperture and relative to both of said arms over a range of different positions of said arms so that said arms can be locked in a range of different positions.

2. A vaginal speculum according to claim 1, wherein said support for said elongate locking member is a pivotal support.

3. A vaginal speculum according to claim 2, wherein said pivotal support of said locking member has sufficient friction to hold said locking member in a range of different positions relative to said one of said handles against the weight of said locking member.

4. A vaginal speculum according to claim 1, wherein said elongate locking member is of a softer material than said arms.

5. A vaginal speculum according to claim 1, wherein said elongate member is a bar of a rectangular section.

6. A vaginal speculum according to claim 5, wherein the width of said first portion of said aperture is wider than said bar and the width of said second portion is narrower than said bar.

7. A vaginal speculum comprising: two arms; a hinge between said two arms at a point along their length such that said two arms are formed into a pair of jaws on one side of said hinge and a pair of handles on an opposite side of said hinge arranged such that said jaws can be separated by squeezing together said handles; an elongate locking bar of a relatively soft plastics material, said locking bar having a first end and a second end; a pivotal support for said first end of said locking bar on one of said handles; an aperture in the other of said handles, said second end of said locking bar extending through said aperture, and said aperture having a first portion shaped to allow free passage therethrough of said locking bar and a second portion narrower than said first portion shaped to grip said locking bar such as to lock said arms with one another, said locking bar being manually displaceable between said first and second portions of said aperture and relative to both of said arms over a range of different positions of said arms so said arms can be locked in a range of different positions.

* * * * *